(12) United States Patent
Napier-Roden (10) Patent No.: US 12,397,073 B2
(45) Date of Patent: Aug. 26, 2025

(54) UVC SANITIZING BAG (71) Applicant: Christyne Napier-Roden, San Jose, CA (US)

(72) Inventor: Christyne Napier-Roden, San Jose, CA (US)

( * ) Notice: Subject to any disclaimer, the term of this patent is extended or adjusted under 35 U.S.C. 154(b) by 456 days.

(21) Appl. No.: 17/871,197

(22) Filed: Jul. 22, 2022

(65) Prior Publication Data
US 2023/0023423 A1 Jan. 26, 2023

Related U.S. Application Data

(63) Continuation-in-part of application No. 29/801,068, filed on Jul. 26, 2021, now Pat. No. Des. 1,030,952.

(60) Provisional application No. 63/224,785, filed on Jul. 22, 2021.

(51) Int. Cl.
*A61L 2/10* (2006.01)
*A61L 2/26* (2006.01)

(52) U.S. Cl.
CPC ........ *A61L 2/10* (2013.01); *A61L 2/26* (2013.01); *A61L 2202/11* (2013.01); *A61L 2202/122* (2013.01); *A61L 2202/14* (2013.01); *A61L 2202/16* (2013.01)

(58) Field of Classification Search
CPC .......... A61L 2/10; A61L 2/26; A61L 2202/11; A61L 2202/122; A61L 2202/14; A61L 2202/16
See application file for complete search history.

(56) References Cited

U.S. PATENT DOCUMENTS

| 8,378,323 | B1 | 2/2013 | Spann et al. | |
| 8,617,464 | B2 * | 12/2013 | Kerr | A61L 2/10 |
| | | | | 422/24 |
| 9,289,527 | B1 * | 3/2016 | Lichtblau | A61L 2/24 |
| 2008/0118395 | A1 | 5/2008 | Benedek | |
| 2012/0006640 | A1 * | 1/2012 | Santy | A45C 13/36 |
| | | | | 190/115 |

(Continued)

FOREIGN PATENT DOCUMENTS

CN 107308475 A * 11/2017 ............... A61L 2/10

OTHER PUBLICATIONS

Doctor's Choice UV Sanitizer Box, retrieved from the internet on Oct. 26, 2022, Amazon Review date Sep. 12, 2020, hereinafter Doctor's Choice (Year: 2020).*

(Continued)

*Primary Examiner* — David E Smith (57) ABSTRACT

The UVC sanitizing bag is a device intended to help with eliminating harmful bacteria and viruses from various solid products. In order to accomplish this, the device includes a bag base that ensures the bag can stay charged and hold various products. Further, the bag lid ensures the product placed within the device can be exposed to UVC lights from multiple directions. Additionally, the plurality of bag handles and bag pockets provide the user with additional functionality and storage. Further, a plurality of boards and shelves are designed to allow multiple storage levels which can be created within the UVC sanitizing bag and ensure the bag retains its overall shape. Thus, the device is a bag that can sanitize any solid product placed within, quickly and efficiently by utilizing UVC lights and ensures the safety of the user throughout the process.

13 Claims, 12 Drawing Sheets

(56) References Cited

U.S. PATENT DOCUMENTS

2015/0181994 A1* 7/2015 Ponx .................. A45C 3/10
                                                    150/118
2018/0154028 A1   6/2018 Offutt et al.
2018/0214585 A1   8/2018 Piper
2020/0368380 A1* 11/2020 Levy .................. A61L 2/10

OTHER PUBLICATIONS

UV-C Sanitizing Light Disinfection Portable Bag: Glow Box 2.0, Retrieved from Internet on Apr. 13, 2021, URL:https://uvclean/house.com/products/uv-c-sanitizing-portable-bag) (Year: 2021).*

Doctor's Choice UV Sanitizer Box, retrieved from the internet on Oct. 26, 2022, Amazon Review date Sep. 12, 2020 (Year: 2020).*

Doctor's Choice UV Sanitizer Box. Personal UV Sterilizer Box. Extra Large UV Light Sanitizer Box fits Masks, Phones, Sleep Aid, Glasses, Bottles, Toothbrush, Pacifier. retrieved from the internet, retrieved on Oct. 26, 2022; <URL: https:// ww.amazon.com/UV%C2%ADSanitizer-Sterilizer-Toothbrush%C2%ADPacifier/dp/B091BC5HND/ref=sr_1_1_sspa?keywords=DOCTOR%27S+CHOICE+UV+STERILIZER&qid=1663617629&sr=8-1-spons&psc=1>.

JJ Care UV Sterilizer Bag, Retrieved from Internet, Retrieved on Apr. 13, 2021 <URL: https://www.ebay.com/itm/284516615211>.

UV-C Sanitizing Light Disinfection Portable Bag, Retrieved from Internet, Retrieved on Apr. 13, 2021 <URL: https://uvcleanhouse.com/products/uv-c-sanitizing-portable-bag>.

JJ Care UV Light Sanitizer Bag, Large UV Sterilizer Bag, Retrieved from Internet, Retrieved on Apr. 13, 2021 <URL: https://www.amazon.in/JJ-CARE-Sterilizer-Multipurpose-Disinfection/dp/B087BT5LFX>.

\* cited by examiner

UVC SANITIZING BAG

FIELD OF THE INVENTION

The present invention relates generally to a sanitizing bag that utilizes UVC (ultraviolet C) lights. More specifically, the present invention is a device that is designed to sanitize any solid product placed within the UVC sanitizing bag.

BACKGROUND OF THE INVENTION

Within this current time period individuals experience and come into contact with many harmful and dangerous bacteria, germs and viruses. Many individuals come into contact with them in public areas, where being near other individuals is unavoidable. Some ways to limit the spread of these dangerous bacteria and viruses is by sanitizing various surfaces and by wearing protective equipment. Although, these methods of limiting the spread of viruses are effective they do not cover all potentially dangerous areas. For example, at a grocery store many individuals will touch and inspect their food before putting it in their cart and buying it, or before replacing it and continuing with their shopping. Certain produce cannot be sanitized in the same manner as other surfaces and thus present a potential way, where harmful bacteria and viruses can be spread from person to person. To mitigate the spread of these harmful bacteria and viruses, individuals must either rely on other people to not touch products if they do not purchase them or must hand clean each item once they are home. Unfortunately, hand cleaning each product is not entirely effective as it might not cover each area and additionally it takes a significant amount of time to properly clean each item. Thus, a small enclosure or bag that can sanitize grocery products in a mess free, quick, and efficient way is a need of the hour.

An objective of the present invention is to provide users with a sanitizing bag, to help eliminate harmful bacteria and viruses from grocery products. The present invention intends to provide users with a device that can hold various items and properly sanitize each item quickly and efficiently by utilizing UVC lights. Ultraviolet C (UVC) is a type of ultraviolet light with wavelengths between 100-280 nanometers (nm). UVC light is a known disinfectant that inactivates viruses and bacteria. Accordingly, a preferred embodiment of the present invention comprises a bag base, a bag lid, a plurality of bag handles, a plurality of bag pockets, and a plurality of boards. Further, the bag lid comprises components that control the various electronics throughout the present invention to ensure the user has a convenient and useful experience. Thus, the present invention is a bag that can sanitize any solid product placed within the bag, quickly and efficiently by utilizing UVC lights and ensures the safety of the user throughout the process.

SUMMARY

An objective of the present invention is to help with eliminating harmful bacteria and viruses from various solid products. In other words, the present invention seeks to provide users with a device that can eliminate harmful bacteria and viruses from solid product by utilizing UVC lights on the top and bottom of a bag. In order to accomplish this the present invention comprises a bag base that ensures the present invention can stay charged and hold various products. Further, the bag lid and bag base ensure that the products placed within the present invention can be exposed to UVC lights from multiple directions. Additionally, the plurality of bag handles and bag pockets provide the user with additional functionality and storage. Further, a plurality of boards and shelves are designed to allow multiple storage levels which can be created within the UVC sanitizing bag and ensure the present invention retains its overall shape. Thus, the present invention is a bag that can sanitize any solid product placed within, quickly and efficiently by utilizing UVC lights while ensuring the safety of the user throughout the process.

DETAIL DESCRIPTIONS OF THE INVENTION

All illustrations of the drawings are for the purpose of describing selected versions of the present invention and are not intended to limit the scope of the present invention. In reference to FIG. 1 through FIG. 12, the present invention is a UVC sanitizing bag. An objective of the present invention is to help with eliminating harmful bacteria and viruses from various solid products. In other words, the present invention seeks to provide users with a device that can eliminate harmful bacteria and viruses from solid product by utilizing UVC lights on the top and bottom of a bag. In order to accomplish this the present invention comprises a bag base that ensures the present invention can stay charged and hold various products. Further, the positioning of the UVC lights within the bag lid and the bag base ensures the product placed within the present invention can be exposed to UVC lights from multiple directions. Additionally, the plurality of bag handles and bag pockets provide the user with additional functionality and storage. Furthermore, a plurality of boards and shelves are designed to allow multiple storage levels which can be created within the UVC sanitizing bag and ensure the present invention retains its overall shape. Thus, the present invention is a bag that can sanitize any solid product placed within, quickly and efficiently by utilizing UVC lights and ensures the safety of the user throughout the process.

Figure 1:
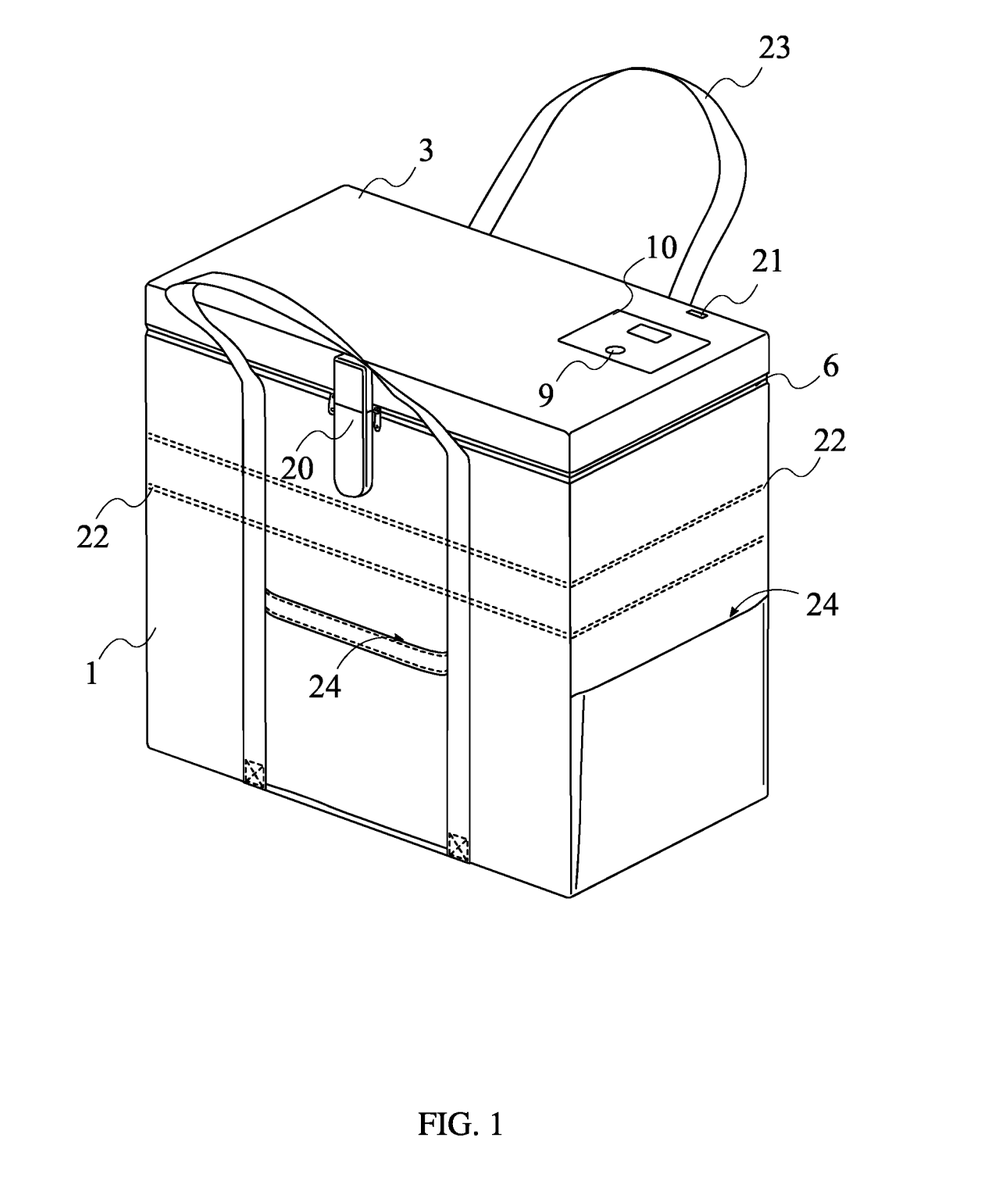
FIG. 1 is a top-front left perspective view of the present invention, wherein the lid is closed.
Figure 2:
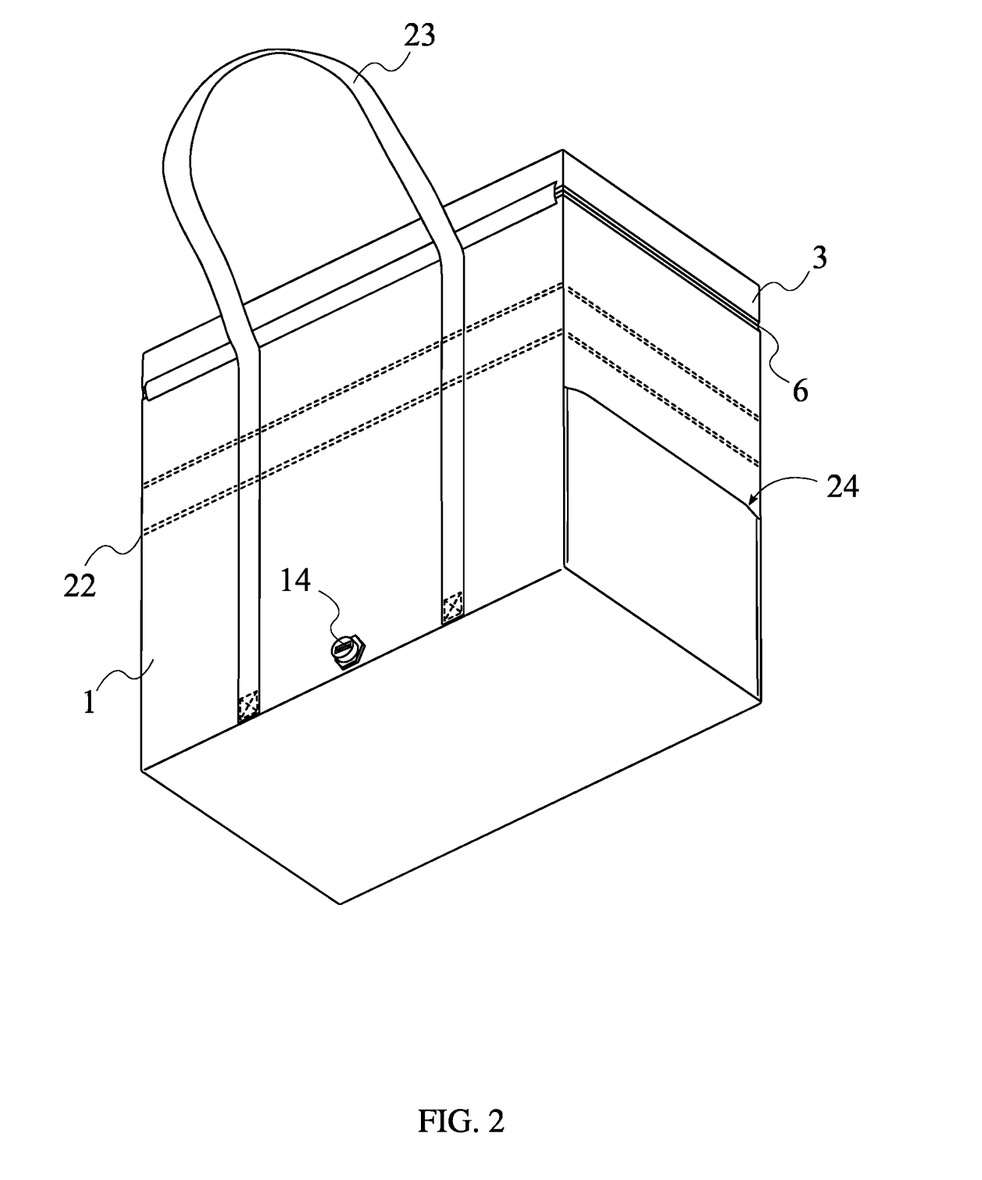
FIG. 2 is a is a bottom rear right perspective view of the present invention, wherein the lid is closed.
Figure 3:
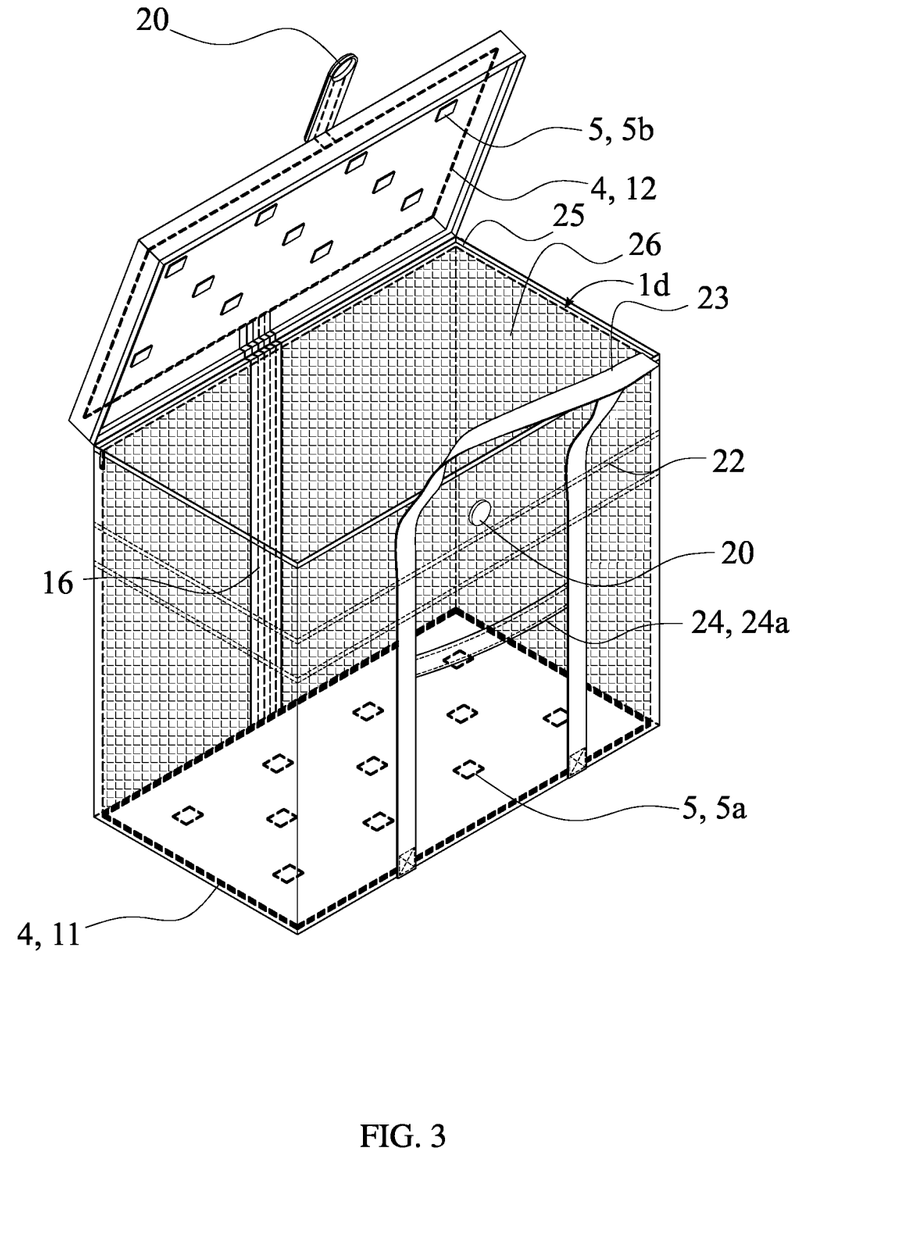
FIG. 3 is a top front right perspective view of the present invention, wherein the lid is open, the trays are not shown, and the bag base is shown in phantom.
Figure 4:
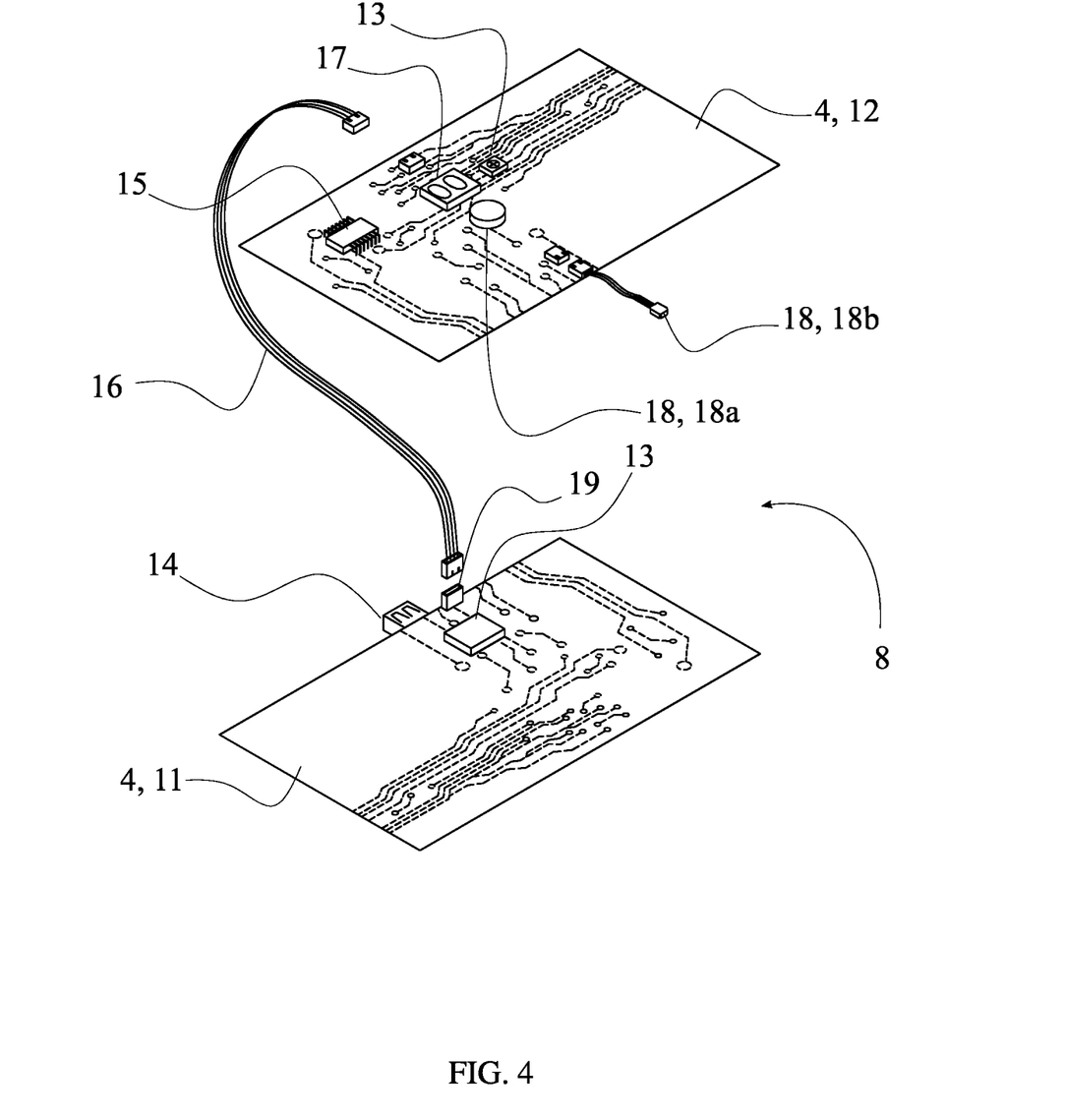
FIG. 4 is a perspective view illustrating the electric and electronic components of the present invention.
Figure 5:
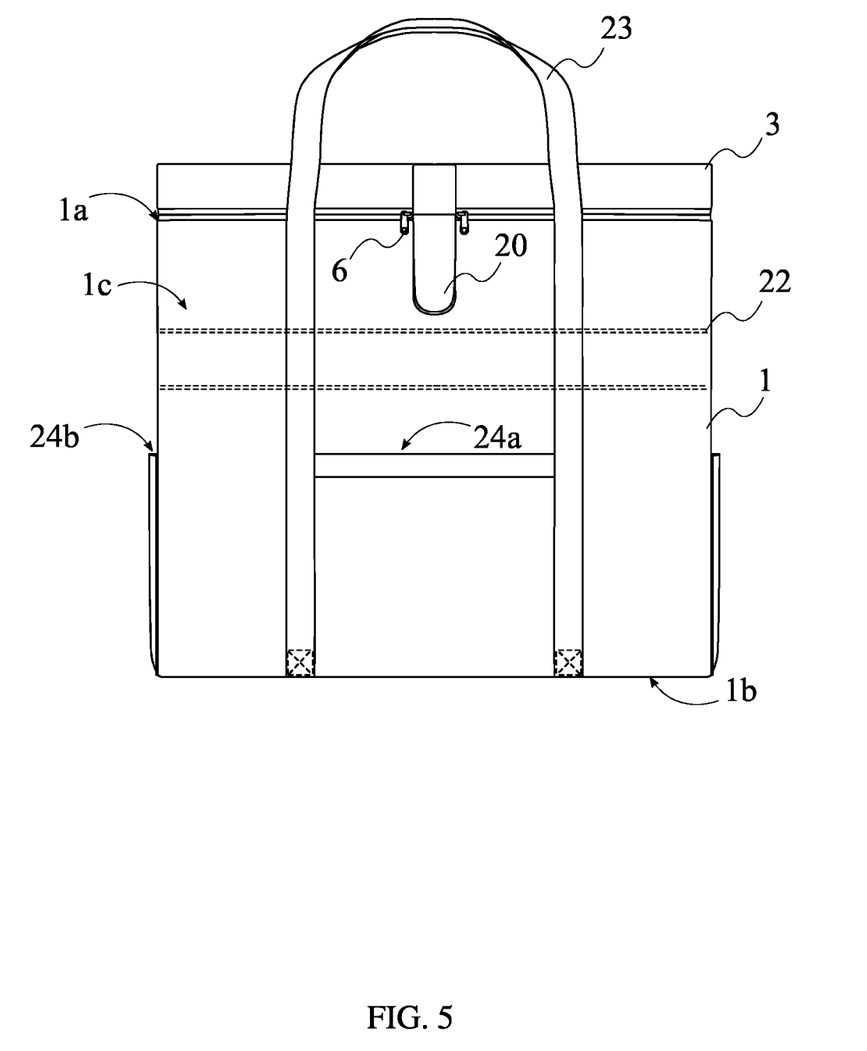
FIG. 5 is a front elevational view of the present invention.
Figure 6:
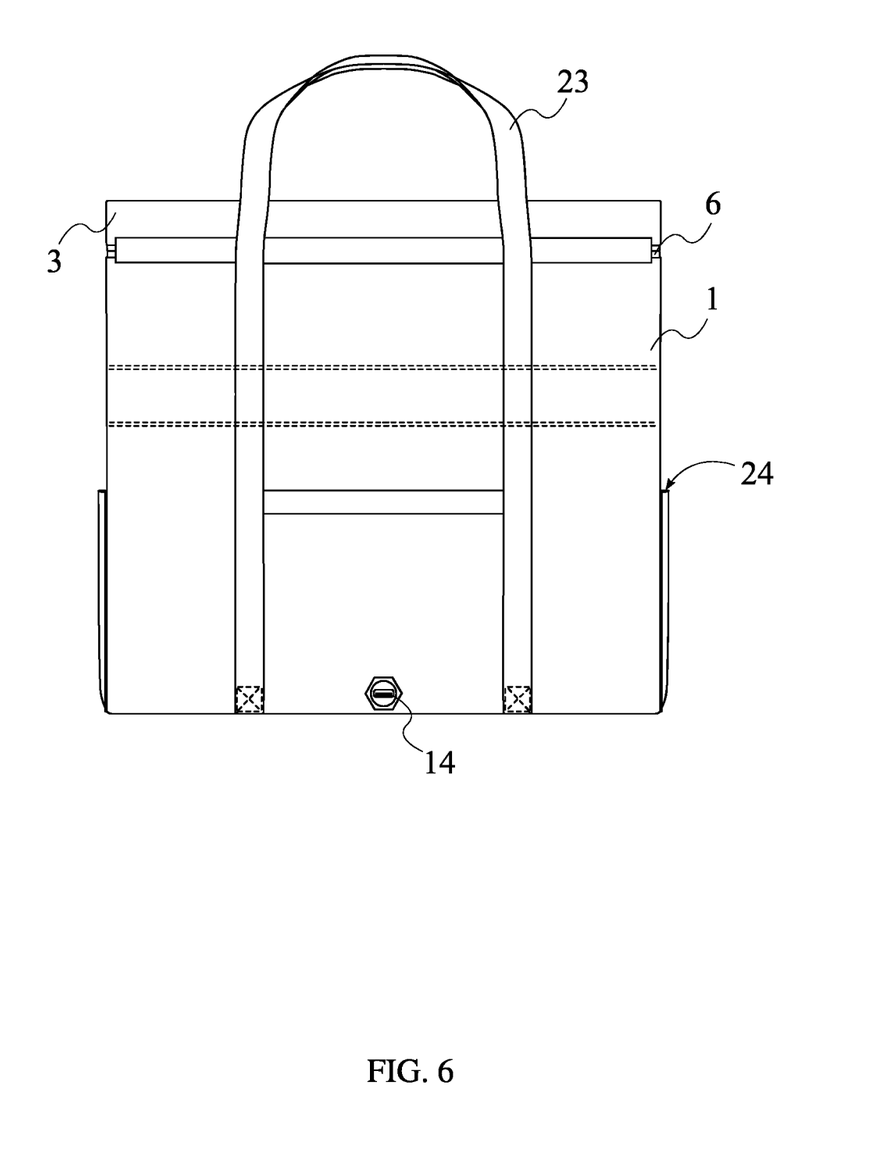
FIG. 6 is a rear elevational view of the present invention.
Figure 7:
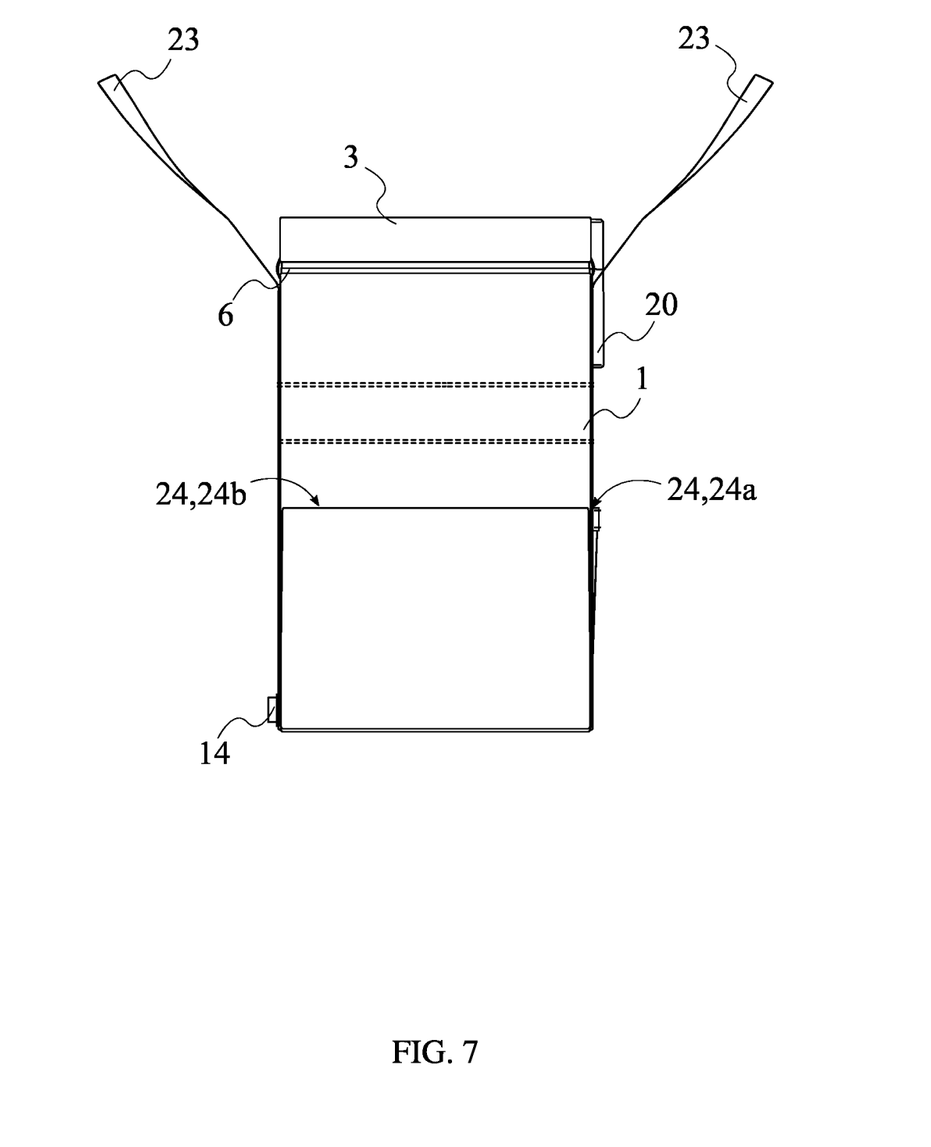
FIG. 7 is a right-side elevational view of the present invention.

The following description is in reference to FIG. 1 through FIG. 12. According to a preferred embodiment, the present invention comprises a receptacle 1, an inner cavity 2, a lid 3, a plurality of PCBs 4 (printed circuit boards), a plurality of UVC light sources 5, a first fastener 6, at least one shelf 7, an electrical system 8, a human interface device (HID) 9, and a display device 10. The receptacle 1 is made of a flexible material, with a hollow rectangular shape with an open top face. To that end, the inner cavity 2 traverses into the receptacle 1, and the inner cavity 2 extends from a first end 1*a* of the receptacle 1 towards a second end 1*b* of the receptacle 1, wherein the first end 1*a* is positioned opposite to the second end 1*b* across the receptacle 1. This is so that, the present invention can hold various products with the inner cavity 2 of the receptacle 1. As seen in FIG. 5, the first end 1*a* constitutes a top end of the receptacle 1 and the second end 1*b* constitutes a bottom end of the receptacle 1. However, the receptacle 1 may comprise any other shape, size, material, components, arrangement of components etc. that are known to one of ordinary skill in the art, as long as the intents of the present invention are not altered. As seen in FIG. 9 through FIG. 12, the lid 3 is hingedly connected to an edge of the receptacle 1 adjacent to the first end 1*a*. In other words, the receptacle 1 connects to the bag lid 3 along the rear side, close to the top end of the bag. When the device is in a working mode, the lid 3 covers the inner cavity 2, as seen in FIG. 1 and FIG. 2. More specifically, the lid 3 covers the open top section of the receptacle 1, when needed. In the preferred embodiment, the plurality of PCBs 4 holds or houses the important electrical and electronic components of the present invention. Preferably, the plurality of PCBs 4 are sturdy rectangular boards made of one or more solid materials that are suitable for housing integrated circuits. As seen in FIG. 4, the plurality of PCBs 4 comprises a first board 11 and a second board 12. Preferably, the first board 11 is mounted within the receptacle 1 adjacent the second end 1*b*, and the second board 12 is mounted within the lid 3.

The present invention is a bag that can sanitize any solid product placed within, quickly and efficiently by utilizing UVC lights. To accomplish this, the plurality of UVC light sources 5 and the electrical system 8 are mounted adjacent the plurality of PCBs 4. Ultraviolet C (UVC) is a type of ultraviolet light with wavelengths between 100-280 nanometers (nm). UVC light is a known disinfectant that inactivates viruses and bacteria. In the preferred embodiment, the plurality of UVC light sources 5 comprises plurality of strips of UVC lights arranged parallelly with respect to each other. This arrangement will ensure that any product placed within the present invention will receive adequate UVC light coverage from opposing ends. However, the plurality of UVC light sources 5 may comprise any other shape, size, location, number, arrangement etc., as long as the intents of the present invention are not altered.

As seen in FIG. 1 and FIG. 2, the first fastener 6 is integrated between the first end 1*a* of the receptacle 1 and the lid 3. This is so that no light traverses out from the receptacle 1 when the lid 3 is fastened to the receptacle 1 with the first fastener 6. In the preferred embodiment, the first fastener 6 is a zipper. The zipper is located around the bottom edge of the front, left and right side of the bag lid 3. The zipper is designed to close the lid 3 onto the bag base or receptacle 1 to ensure the UVC light within both components cannot shine onto items outside of the present invention, thereby ensuring safety of users. However, the first fastener 6 may comprise any other fastening mechanism, size, technique etc. that are known to one of ordinary skill in the art, as long as the objectives of the present invention are not hindered.

In order to hold or house the products that need to be sanitized safely within the receptacle 1, the at least one shelf 7 is mounted within the inner cavity 2, not touching the plurality of UVC light sources 5. Preferably, the at least one shelf 7 allows various items to lay within the inner cavity 2, while still being exposed to the plurality of UVC light sources 5. To accomplish this, the at least one shelf 7 comprises a grid structure, is made of a reflective material, and comprises a transverse cross section that is similar to that of the receptacle 1. This is so that light easily passes through the grid, gets reflected with the help of the reflective material, and the at least one shelf 7 sits firmly within the dimensions of the inner cavity 2. However, the at least one shelf 7 may comprise any other shape, size, material, location, components, arrangement of components etc., as long as the intents of the present invention are fulfilled.

Figure 8:
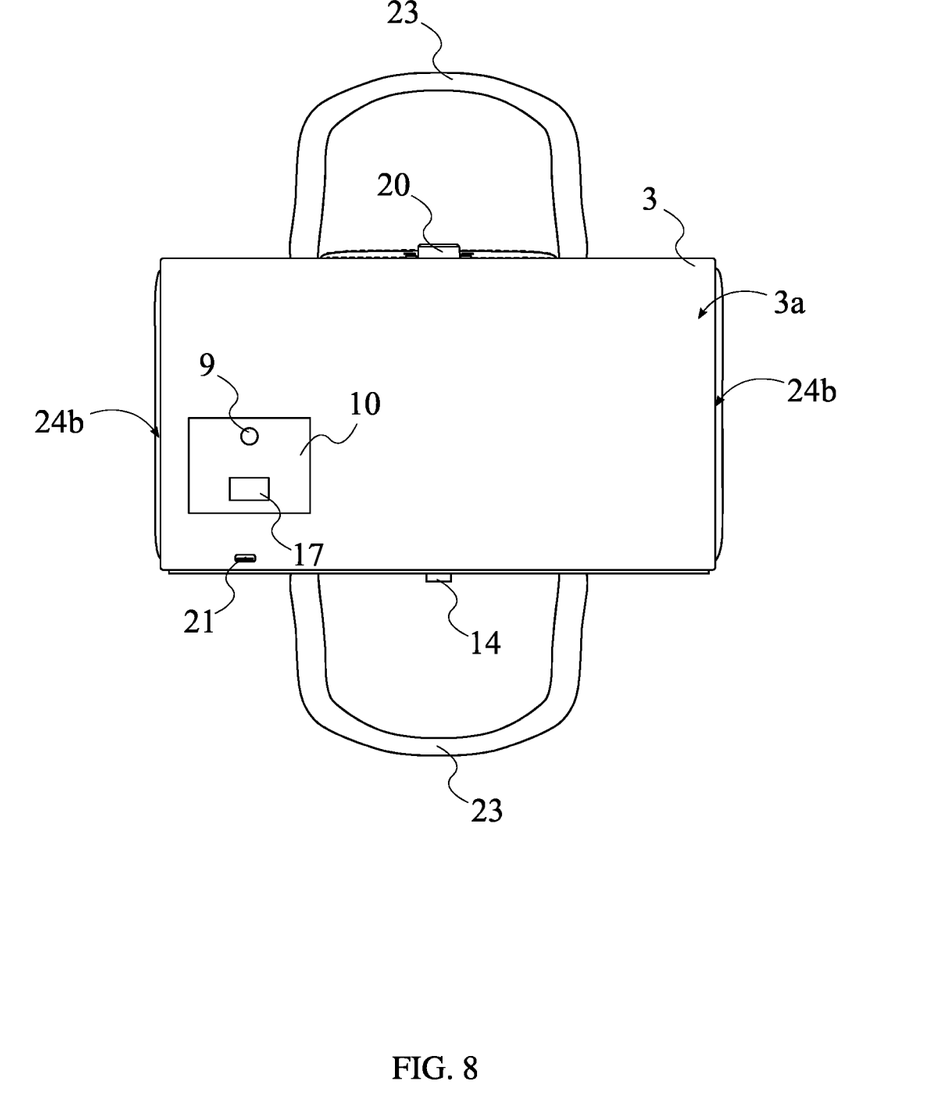
FIG. 8 is a top plan view of the present invention.
Figure 9:
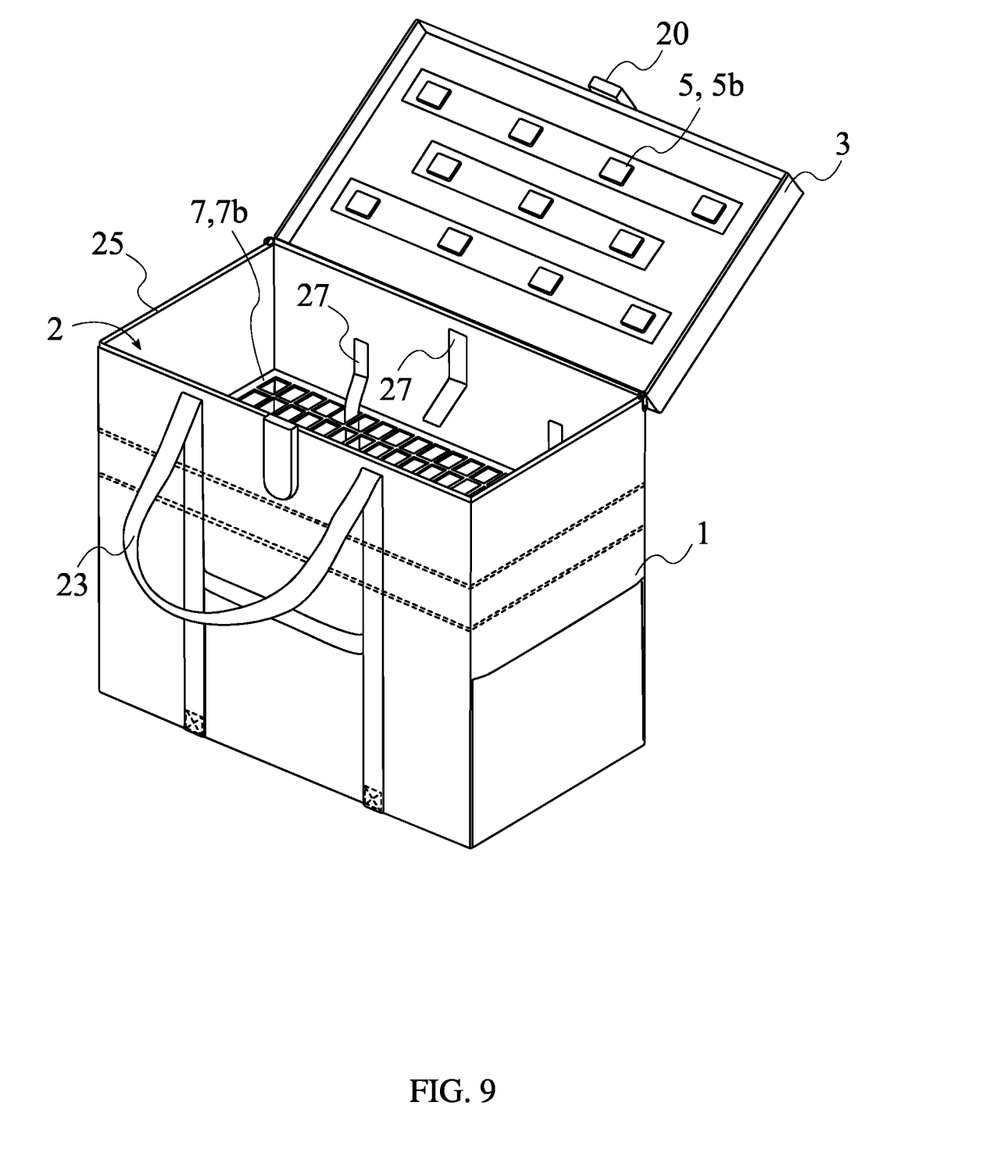
FIG. 9 is a top front left perspective view of the present invention, wherein the lid is open.
Figure 10:
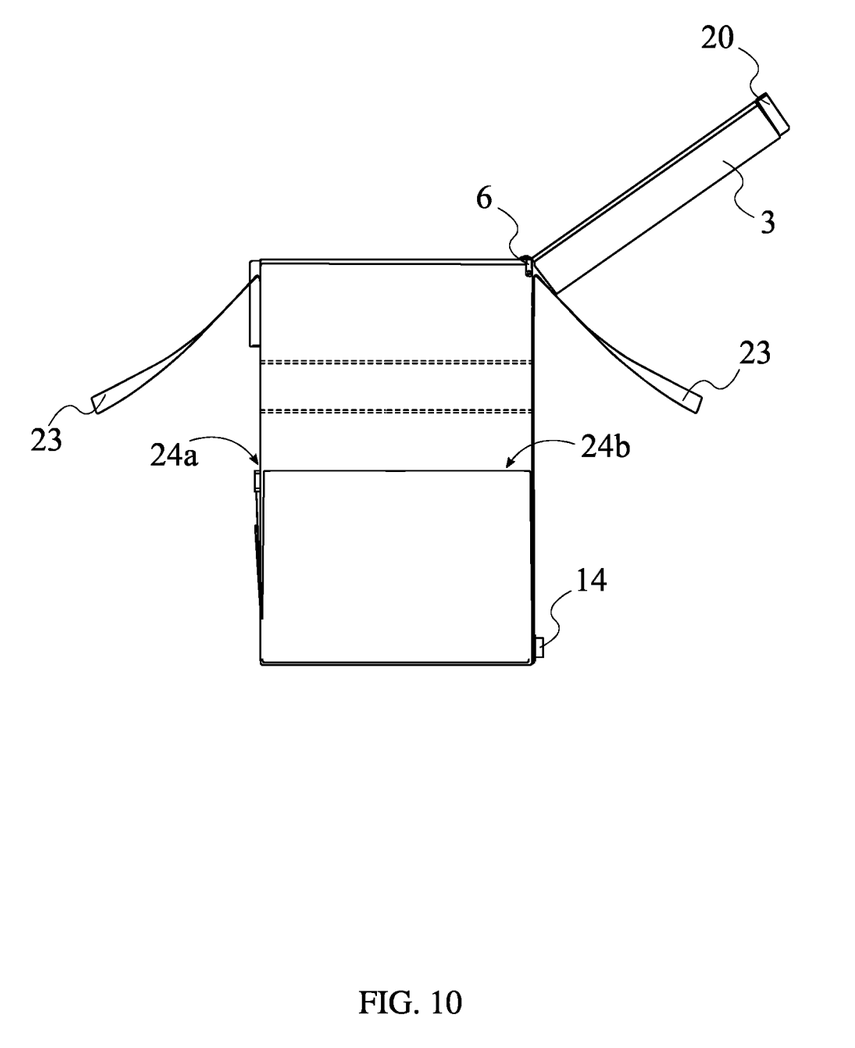
FIG. 10 is a left side elevational view, wherein the lid is open.

According to the preferred embodiment, the electrical system 8 comprises a plurality of electrical and electronic components that work together for the smooth functioning of the present invention. To that end, the plurality of UVC light sources 5 and the HID 9 are electronically connected to the electrical system 8, wherein actuating the electrical system 8 initiates actuation of the plurality of UVC light source, which in turn initiates a sanitization process of products placed within the inner cavity 2. As seen in FIG. 8, the HID 9 and the display device 10 are mounted onto an external surface 3*a* of the lid 3. Preferably, the HID 9 is an ON/OFF button that when pressed will directly cut off or open current flowing to the electrical components of the present invention, to ensure the present invention can be easily turned on and off. Thus, in effect the HID 9 is operably coupled to the plurality of UVC lights 5, wherein operating the HID 9 governs actuation of the plurality of UVC lights 5. Further, the display device 10 is electronically coupled to the electrical system 8, wherein the display device 10 displays the actuation and progress status of the sanitization process. Preferably, the display device 10 is an OLED display SSD1306 that serves as a user interface to relay various information to the user. However, the display device 10 and the HID 9 may comprise any other size, brand, technology, etc. that are known to one of ordinary skill in the art, as long as the intents of the present invention are fulfilled.

A more detailed description of the present invention follows. As seen in FIG. 3, the plurality of UVC light sources 5 comprises a first set of lights 5*a* and a second set of lights 5*b*. Preferably, the first set of lights 5*a* are mounted adjacent the first board 11, and the second set of lights 5*b* are mounted adjacent the second board 12, wherein the first set of lights 5*a* and the second set of lights 5*b* are oriented towards the inner cavity 2. In other words, the plurality of UVC light sources 5 is mounted at both the top and bottom ends of the present invention. This is so that the products placed within the receptacle 1 are efficiently sanitized with the help of UVC lights from different angles.

In order to accomplish the smooth functioning of the present invention, the electrical system 8 comprises a power source 13, a charging port 14, a processor 15, a main connecting wire 16, a timer 17, and at least one sensor 18. As seen in FIG. 4, the power source 13 and the charging port 14 are mounted onto the first board 11. Further, the processor 15, the timer 17, and the at least one sensor 18 are mounted onto the second board 12. Preferably, the power source 13 is a rechargeable battery. The battery is designed as a slim rectangular shape and has preferably a 5000 mAh capacity but is not limited to this size. However, any other power sources may be used, as long as the intents of the present invention are not altered. Examples of such power sources include, but are not limited to solar power, Li batteries, power from power outlets, external batteries etc. As the present invention is charged by the charging port 14 the battery located above the first board 11, retains most of the electricity for later use. Located on the rear side of the first board 11 is the charging port 14 which is designed as a USB-C to ensure the present invention can be charged by an outside electrical source quickly and easily seen in FIG. 2. However, the charging port 14 may comprise any other size, shape, type etc. as long as the intents of the present invention are fulfilled.

The processor 15 controls the actions of all the electronic components of the present invention. For example, the processor 15 will control other electronics within the present invention such as controlling the HID 9, any indicator LED light, indicate the user to properly shut the bag lid through the displace device 10 etc., amongst various other information. To accomplish this, the processor 15 and the charging port 14 are electrically connected to the power source 13.

As seen in FIG. 3 and FIG. 4, along the rear side of the receptacle 1 is the main connector wire 16. The main connector wire 16 ensures that electricity can flow between the bad lid and the bag base. In other words, the main connecting wire 16 is electrically connected between the first board 11 and the second board 12. Connected at the bottom of the main connector wire 16 is the first board 11 that is designed to control and relay information to the base UVC light or the first set of lights 5a. The first board 11 comprises the charging port 14 and a connection plug 19, as shown in FIG. 4. The connection plug 19 is preferably a JST connector plug that allows both information and electricity to flow from the main connector wire to the first board 11 and back.

According to the preferred embodiment, the at least one sensor 18 and the timer 17 are electronically connected to the processor 15. The timer 17 is preferably a digital timer that may be seen at the top of the present invention that indicates the amount of time left for the product within the present invention to become properly sanitized. The at least one sensor 18 is intended to sense user presence and prevent unexpected UVC light exposure from within the present invention. In the preferred embodiment, the at least one sensor 18 comprises a digital capacitive touch sensor 18a that is operably coupled with the HID 9, and a magnetic catch safety clasp sensor 18b, that is operably coupled to a second fastener 20. Preferably, the second sensor 20 is a magnetic safety clasp that is mounted between the receptacle 1 and the lid 3. More specifically, the second fastener 20 is operably connected to the at least one sensor 18 (18b), wherein operating the second fastener 20 enables shutting down of the sanitization process. This component is designed so that once the magnetic connection is broken the present invention will automatically turn off to ensure that the user will not accidentally be exposed to any UVC light.

As seen in FIG. 1 and FIG. 8, the present invention comprises a USB (universal serial bus) charging port 21. Preferably, the USB charging port 21 is mounted onto the lid, and the USB charging port 21 is electrically connected to the second board 12. The USB charging port 21 utilizes the power from the power source 13 to allow the user to charge their phone or another electronic device with the present invention.

It should be noted that any other electric and electronic components, (for e.g., connection wires, ICs (integrated circuits) etc.) that are known to one of ordinary skill in the art, may be included and will fall under the scope of the present invention, as long as the intents of the present invention are not hindered.

Continuing with the preferred embodiment, the present invention comprises a plurality of reinforcement straps 22, and a plurality of bag handles 23. Preferably, the plurality of reinforcement straps 22 is laterally mounted around receptacle 1. In other words, as seen in FIG. 1 and FIG. 2, around the outer sides of the receptacle 1 are the plurality of reinforcement straps 22 designed as long thin cylindrical lines that can help keep the receptacle 1 in its hollow rectangular shape. Further, the plurality of bag handles 23 is mounted on opposing sides of the receptacle 1 adjacent the first end 1a. The plurality of bag handles 23 is designed with a sturdy material that creates an upside-down U-shape to allow the user to easily and efficiently carry the present invention.

As seen in FIG. 1, FIG. 2, FIG. 5 etc., the present invention comprises a plurality of pockets 24. Preferably, the plurality of pockets 24 is laterally mounted onto an external surface 1c of the receptacle 1. In its preferred embodiment the plurality of bag pockets 24 comprises a front pocket 24a and a plurality of side pockets 24b. The front pocket 24a is positioned in between the U-shaped bag handle on the front side of the receptacle 1 as shown in FIG. 5. The front pocket 24a is designed with a rectangular shape to create a space for the user to place a phone or electronic device. Shown in FIG. 5, along the left and right side of the bag base the plurality of side pockets 24b is positioned. The plurality of side pockets 24b is designed as larger rectangular shapes that allow for extra storage for the present invention. It should be noted that the plurality of bag handles 23 and the plurality of pockets 24 may comprise any other shape, size, location, material etc., as long as the intents of the present invention are fulfilled.

As seen in FIG. 3, the present invention comprises a plurality of reinforcement boards 25. Preferably, the plurality of reinforcement boards 25 is laterally integrated around the sidewalls of the present invention. More specifically, the plurality of reinforcement boards 25 is located on the top, bottom, front, and rear side of the present invention shown in FIG. 3. In the preferred embodiment, the plurality of reinforcement boards 25 comprises rectangular panels made of a cardboard material, shaped to match each side of receptacle 1 of the present invention. This design allows the present invention to hold various objects while still retaining its original shape seen in FIG. 1, while also being slightly flexible. However, the plurality of reinforcement boards 25 may comprise any other material, size, shape, components, arrangement of components etc., as long as the objectives of the present invention are fulfilled.

According to the preferred embodiment, the present invention comprises an insulation layer 26. Preferably, the insulation layer 26 is mounted laterally along inner sidewalls 1d of the receptacle 1. The insulation layer 26 is a protective measure to ensure that none of the UVC light reaches outside of the bag to ensure the user is not exposed to potentially harmful UVC light seen in FIG. 3. Further, the insulation layer 26 is also made of a reflective material, so that UVC light falling on the inner sidewalls 1d may be reflected and the products placed within the inner cavity 2 gets sanitized by multiple angles.

Figure 11:
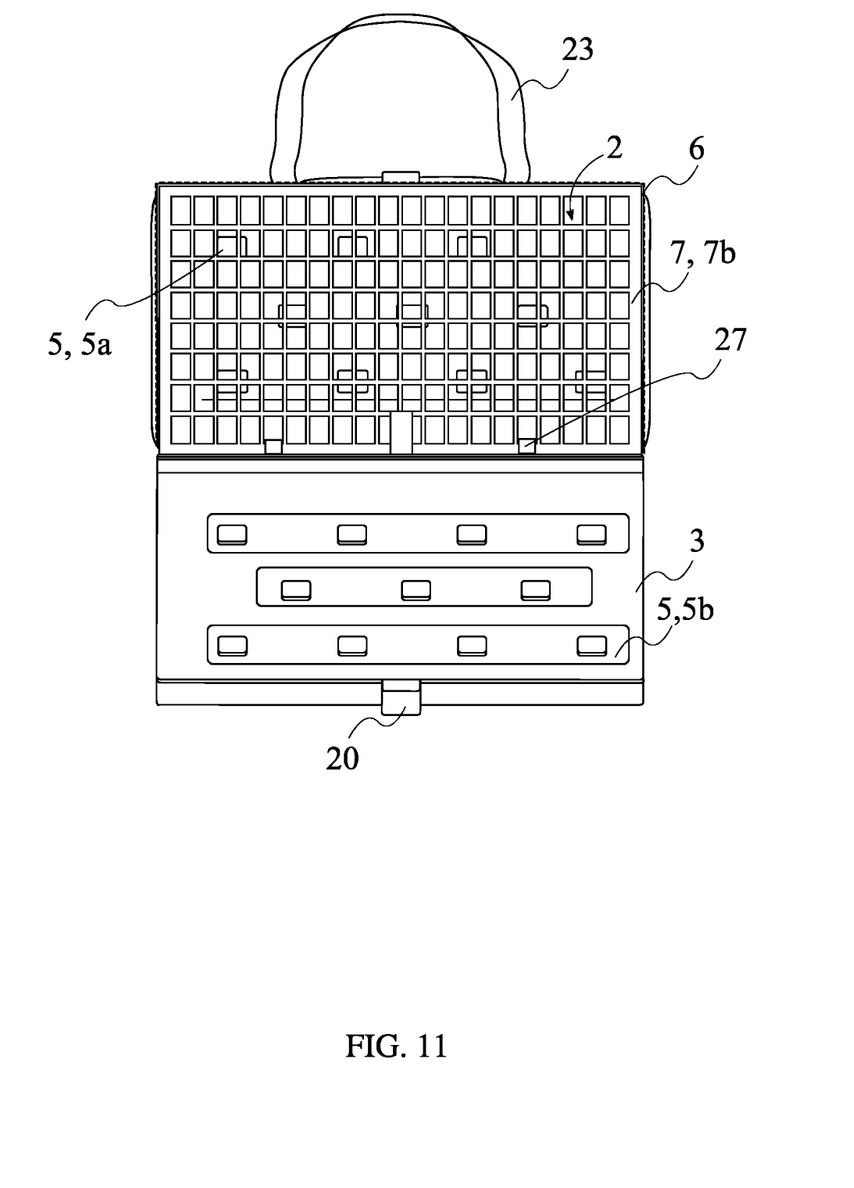
FIG. 11 is a top plan view of the present invention, with the lid open.
Figure 12:
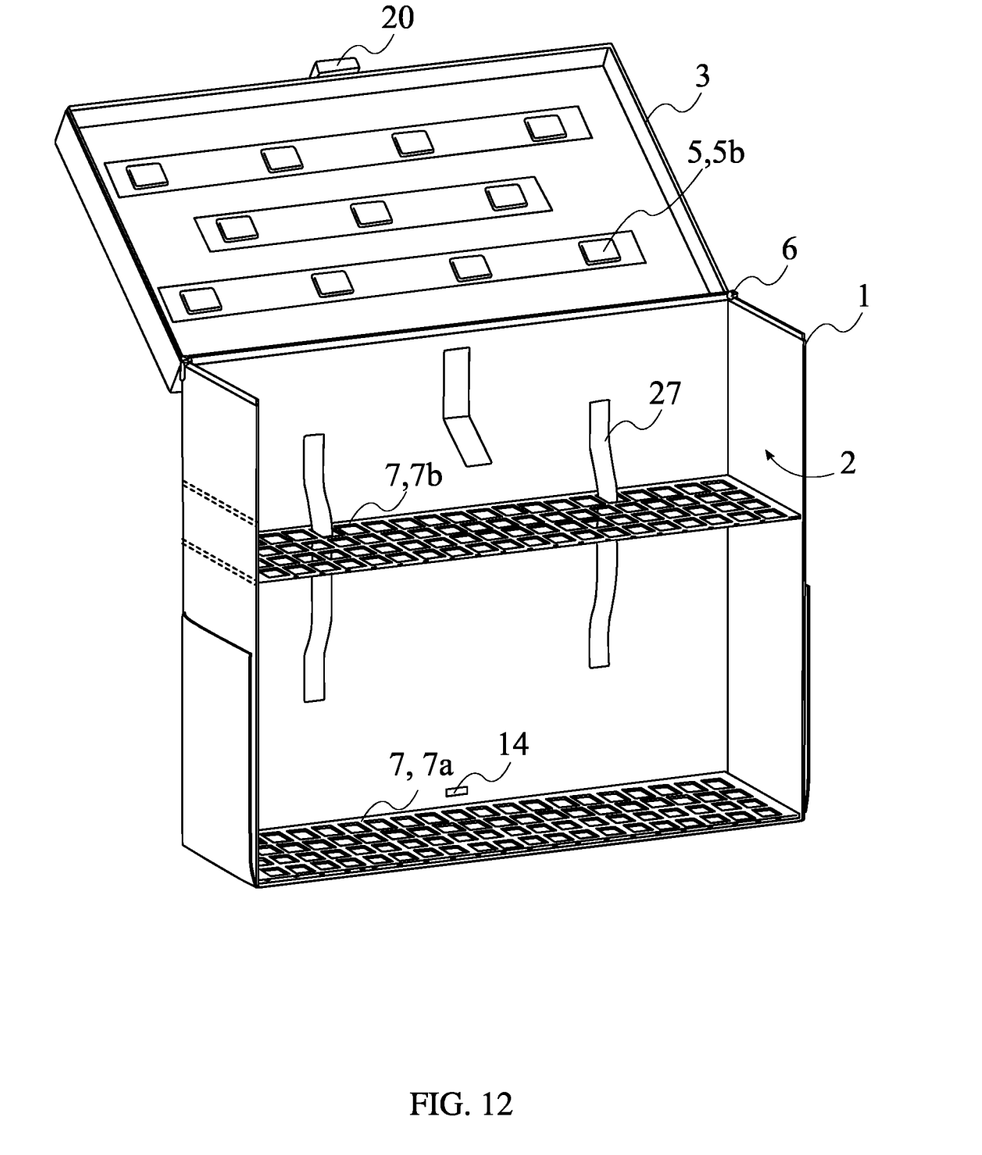
FIG. 12 is a top front sectional view of the present invention, wherein the lid is open.

In reference to FIG. 12, the at least one shelf 7 comprises a first shelf 7a and a second shelf 7b. Preferably, the first shelf 7a is mounted within the inner cavity 2 adjacent the second end 1b. The first shelf 7a allows various items to lay on the bottom of the bag base while still being exposed to the base UVC lights. To ensure the first shelf 7a is not sitting on the first board 11 and hindering with the operation of the electrical components, the first shelf 7a is mounted slightly above the first board 11. In other words, the first shelf 7a is laterally offset from the first board 11. Directly above the first shelf 7a is another divider which is the midway shelf or the second shelf 7b. The second shelf 7b is mounted within the inner cavity 2 and laterally offset from the first shelf 7a. In the preferred embodiment, the second shelf 7b may be folded. To accomplish this, the present invention comprises a plurality of third fasteners 27, wherein the plurality of second fasteners 27 is mounted onto inner sidewalls 1d of the receptacle 1. Further, as seen in FIG. 11, the second shelf 7b is held on normally to the inner sidewalls 1d by the plurality of third fasteners 27. When the plurality of third fasteners 27 is unfastened, the second shelf 7b is foldable along the inner sidewalls 1d of the receptacle 1. In other words, this design allows the second shelf 7b to be disconnected from the receptacle 1 and folded up against the side easily to that the interior of the bag base can be quickly and easily organized. As seen in FIG. 11 and FIG. 12, the plurality of third fasteners 27 comprises hook and loop fasteners. However, any other fastener or fastening technology may be used for the plurality of third fasteners 27, as long as the intents of the present invention are not hindered.

With all the components working in tandem with each other it can be seen that the present invention is a bag that can sanitize any solid product places within quickly and efficiently by utilizing UVC lights and ensures the safety of the user throughout the process.

Although the invention has been explained in relation to its preferred embodiment, it is to be understood that many other possible modifications and variations can be made without departing from the spirit and scope of the invention as hereinafter claimed.

What is claimed is:

1. A UVC (ultraviolet C) sanitizing bag, comprising:
a receptacle;
an inner cavity;
a lid;
a plurality of printed circuit boards (PCBs);
a plurality of UVC light sources;
a first fastener;
at least one shelf;
an electrical system;
a human interface device (HID);
a display device;
the plurality of PCBs comprising a first board and a second board;
the inner cavity traversing into the receptacle;
the inner cavity extending from a first end of the receptacle towards a second end of the receptacle, wherein the first end is positioned opposite to the second end across the receptacle;
the lid being hingedly connected to an edge of the receptacle adjacent to the first end;
the lid covering the inner cavity;
the first board being mounted within the receptacle adjacent the second end;
the second board being mounted within the lid;
the plurality of UVC light sources and the electrical system being mounted adjacent the plurality of PCBs;
the first fastener being integrated between the first end of the receptacle and the lid, wherein no light traverses out from the inner cavity when the lid is fastened to the receptacle with the first fastener;
the at least one shelf being mounted within the inner cavity, not touching the plurality of UVC light sources;
the plurality of UVC light sources and the HID being electronically connected to the electrical system, wherein actuating the UVC lights initiates a sanitization process of products placed within the inner cavity;
the HID and the display device being mounted onto an external surface of the lid;
the HID being operably coupled to the plurality of UVC lights, wherein operating the HID governs actuation of the plurality of UVC lights;
the display device being electronically coupled to the electrical system, wherein the display device displays actuation and progress status of the sanitization process;
a power source, a charging port, a processor, a main connecting wire, a timer, and at least one sensor;
the power source and the charging port being mounted onto the first board;
the processor, the timer, and the at least one sensor being mounted onto the second board;
the processor and the charging port being electrically connected to the power source;
the main connecting wire being electrically connected between the first board and the second board;
the at least one sensor and the timer being electronically connected to the processor;
a second fastener;
the second fastener being operably connected to the at least one sensor, wherein disconnecting the second fastener from the at least one sensor enables shutting down of the sanitization process;
a plurality of reinforcement boards;
the plurality of reinforcement boards being laterally integrated around the sidewalls of the receptacle;
an insulation layer; and
the insulation layer being mounted laterally along inner sidewalls of the receptacle, wherein the insulation layer being reflective.

2. The UVC sanitizing bag of claim 1, comprising:
the plurality of UVC light sources comprising a first set of lights and a second set of lights;
the first set of lights being mounted adjacent the first board;
the second set of lights being mounted adjacent the second board; and
the first set of lights and the second set of lights being oriented towards the inner cavity.

3. The UVC sanitizing bag of claim 1, comprising:
a USB (universal serial bus) charging port;
the USB charging port being mounted onto the lid; and
the USB charging port being electrically connected to the second board.

4. The UVC sanitizing bag of claim 1, comprising:
a plurality of reinforcement straps;
a plurality of bag handles;
the plurality of reinforcement straps being laterally mounted around the receptacle; and
the plurality of bag handles being mounted on opposing sides of the receptacle adjacent the first end.

5. The UVC sanitizing bag of claim 1, comprising:
a plurality of pockets; and
the plurality of pockets being laterally mounted onto an external surface of the receptacle.

6. The UVC sanitizing bag of claim 1, the at least one shelf comprising:
a first shelf and a second shelf;
the first shelf being mounted within the inner cavity adjacent the second end;
the first shelf being laterally offset from the first board; and the second shelf being mounted within the inner cavity and laterally offset from the first shelf.

7. The UVC sanitizing bag of claim 6, comprising:
a plurality of third fasteners;
the plurality of third fasteners being mounted onto inner sidewalls of the receptacle;
the second shelf being held on normally to the inner sidewalls by the plurality of third fasteners; and
the second shelf being folded along the inner sidewalls of the receptacle, wherein the plurality of third fasteners is unfastened.

8. The UVC sanitizing bag of claim 1, wherein the at least one shelf being a grid structure.

9. The UVC sanitizing bag of claim 1, wherein:
the at least one shelf is reflective-; and
the at least one shelf is configured to reflect the plurality of UVC light sources within the inner cavity.

10. A UVC (ultraviolet C) sanitizing bag, comprising:
a receptacle;
an inner cavity;
a lid;
a plurality of printed circuit boards (PCBs);
a plurality of UVC light sources;
a first fastener;
at least one shelf;
an electrical system;
a human interface device (HID);
a display device;
the plurality of PCBs comprising a first board and a second board;
the plurality of UVC light sources comprising a first set of lights and a second set of lights;
the inner cavity traversing into the receptacle;
the inner cavity extending from a first end of the receptacle towards a second end of the receptacle, wherein the first end is positioned opposite to the second end across the receptacle;
the lid being hingedly connected to an edge of the receptacle adjacent to the first end;
the lid covering the inner cavity;
the first board being mounted within the receptacle adjacent the second end;
the second board being mounted within the lid;
the plurality of UVC light sources and the electrical system being mounted adjacent the plurality of PCBs;
the first set of lights being mounted adjacent the first board;
the second set of lights being mounted adjacent the second board;
the first set of lights and the second set of lights being oriented towards the inner cavity;
the first fastener being integrated between the first end of the receptacle and the lid, wherein no light traverses out from the receptacle when the lid is fastened to the receptacle with the first fastener;
the at least one shelf being mounted within the inner cavity, not touching the plurality of UVC light sources;
the plurality of UVC light sources and the HID being electronically connected to the electrical system, wherein actuating the UVC lights initiates a sanitization process of products placed within the inner cavity;
the HID and the display device being mounted onto an external surface of the lid;
the HID being operably coupled to the plurality of UVC lights, wherein operating the HID governs actuation of the plurality of UVC lights;
the display device being electronically coupled to the electrical system, wherein the display device displays actuation and progress status of the sanitization process;
a power source, a charging port, a processor, a main connecting wire, a timer, and at least one sensor;
the power source and the charging port being mounted onto the first board;
the processor, the timer, and the at least one sensor being mounted onto the second board;
the processor and the charging port being electrically connected to the power source;
the main connecting wire being electrically connected between the first board and the second board;
the at least one sensor and the timer being electronically connected to the processor;
a second fastener;
the second fastener being operably connected to the at least one sensor, wherein disconnecting the second fastener from the at least one sensor enables shutting down of the sanitization process;
an insulation layer; and
the insulation layer being mounted laterally along the inner sidewalls of the receptacle.

11. The UVC sanitizing bag of claim 10, comprising:
a plurality of reinforcement straps;
a plurality of bag handles;
a plurality of pockets;
a plurality of reinforcement boards;
the plurality of reinforcement straps being laterally integrated around the receptacle;
the plurality of bag handles being mounted on opposing sides of the receptacle adjacent the first end;
the plurality of pockets being laterally mounted onto the external surface of the receptacle; and
the plurality of reinforcement boards being laterally mounted around the sidewalls of the receptacle.

12. The UVC sanitizing bag of claim 10, the at least one shelf comprising:
a first shelf and a second shelf;
the first shelf being mounted within the inner cavity adjacent the second end;
the first shelf being laterally offset from the first board; and
the second shelf being mounted within the inner cavity and laterally offset from the first shelf.

13. The UVC sanitizing bag of claim 12, comprising:
a plurality of third fasteners;
the plurality of third fasteners being mounted onto lateral inner sidewalls of the receptacle;
the second shelf being held on normally to the inner sidewalls by the plurality of third fasteners; and
the second shelf being foldable along the inner sidewalls of the receptacle.

* * * * *